(12) United States Patent
McKay

(10) Patent No.: US 7,563,455 B2
(45) Date of Patent: Jul. 21, 2009

(54) HIGHLY-MINERALIZED OSTEOGENIC SPONGE COMPOSITIONS, AND USES THEREOF

(75) Inventor: William F. McKay, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 598 days.

(21) Appl. No.: 09/923,116

(22) Filed: Aug. 6, 2001

(65) Prior Publication Data

US 2002/0082694 A1 Jun. 27, 2002

Related U.S. Application Data

(63) Continuation of application No. PCT/US00/03043, filed on Feb. 4, 2000.

(60) Provisional application No. 60/118,615, filed on Feb. 4, 1999.

(51) Int. Cl.
*A61F 2/28* (2006.01)
*A61F 2/00* (2006.01)
*A61F 2/44* (2006.01)

(52) U.S. Cl. .......... 424/428; 623/17.11; 623/23.61

(58) Field of Classification Search .......... 435/252, 435/235; 530/350; 424/422, 423, 420, 93.21, 424/44, 426, 548, 549, 484; 623/17.11, 23.56, 623/17.16; 523/115; 514/12, 44; 606/60, 606/61

See application file for complete search history.

(56) References Cited

U.S. PATENT DOCUMENTS

| | | | | |
|---|---|---|---|---|
| 4,394,370 A | | 7/1983 | Jefferies | 424/15 |
| 4,516,276 A | | 5/1985 | Mittelmeier et al. | 3/1.91 |
| 4,743,229 A | | 5/1988 | Chu | 604/82 |
| 4,776,890 A | | 10/1988 | Chu | 106/161 |
| 4,780,450 A | | 10/1988 | Sauk et al. | 514/2 |
| 4,795,804 A | * | 1/1989 | Urist | 530/350 |
| 4,865,602 A | | 9/1989 | Smestad et al. | 623/16 |
| 4,888,366 A | * | 12/1989 | Chu et al. | 523/115 |
| 4,992,226 A | | 2/1991 | Piez et al. | 264/109 |
| 5,001,169 A | | 3/1991 | Nathan et al. | 523/113 |
| 5,035,715 A | | 7/1991 | Smestad et al. | 623/16 |
| 5,106,626 A | * | 4/1992 | Parsons et al. | 424/423 |
| 5,123,925 A | * | 6/1992 | Smestad et al. | 424/422 |
| 5,231,169 A | * | 7/1993 | Constantz et al. | 530/356 |
| 5,246,457 A | | 9/1993 | Piez et al. | 623/16 |
| 5,273,964 A | | 12/1993 | Lemons | 514/2 |
| 5,425,770 A | | 6/1995 | Piez et al. | 623/16 |
| 5,573,771 A | * | 11/1996 | Geistlich et al. | 424/422 |
| 5,702,449 A | * | 12/1997 | McKay | 623/17.16 |
| 5,776,193 A | | 7/1998 | Kwan et al. | 623/16 |
| 5,785,710 A | * | 7/1998 | Michelson | 606/61 |
| 5,874,109 A | * | 2/1999 | Ducheyne et al. | 424/486 |
| 5,972,368 A | * | 10/1999 | McKay | 424/423 |

FOREIGN PATENT DOCUMENTS

| | | |
|---|---|---|
| EP | 0309241 A2 | 3/1989 |
| EP | 0530804 A1 | 3/1993 |
| EP | 0747067 A2 | 12/1996 |
| WO | WO89/04646 | 6/1989 |
| WO | WO96/39203 | 12/1996 |
| WO | WO97/31661 | 9/1997 |
| WO | WO97/40137 | 10/1997 |
| WO | WO98/17330 | 4/1998 |

* cited by examiner

*Primary Examiner*—Emily M. Le
(74) *Attorney, Agent, or Firm*—Woodard, Emhardt, Moriarty, McNett & Henry LLP

(57) ABSTRACT

Osteogenic sponge compositions having enhanced osteoinductive properties for use in bone repair are described. The compositions include a quickly resorbable porous carrier, a more slowly resorbed mineral scaffold and an osteogenic factor, preferably a bone morphogenetic protein. The compositions enable increased osteoinductive activity while retaining a reliable scaffold for the formation of new bone at an implant site. Methods for therapeutic use of the compositions are also described.

20 Claims, 2 Drawing Sheets

HIGHLY-MINERALIZED OSTEOGENIC SPONGE COMPOSITIONS, AND USES THEREOF

REFERENCE TO RELATED APPLICATION

This application is a continuation of international application number PCT US00/03043, filed Feb. 4, 2000, which claims the benefit of U.S. Patent Application Ser. No. 60/118,615 filed Feb. 4, 1999.

FIELD OF THE INVENTION

The present invention relates generally to osteogenic compositions. Specifically, the present invention relates to an osteogenic sponge composition effective for the induction of new bone growth in animals.

BACKGROUND OF THE INVENTION

Bone grafting has been commonly used to augment healing in the treatment of a broad range of musculoskeletal disorders. This procedure has several disadvantages. If the bone material is obtained from donors of the same species, such as an allograft, an increased risk of disease transmission and immune reaction exists. Bone material surgically removed from the patient, known as an autograft, is also undesirable because a sufficient amount of autogenous bone may not be available and the additional surgery necessary to obtain the autograft increases the risk of infection.

Due to the need for safer bone graft materials, efforts have been directed to finding bone graft substitutes. Candidate compositions include collagen and a bioceramic, such as hydroxyapatite, as these components are the chief structural materials in bone tissue. Bioceramics provide a porous matrix which encourages some new bone growth but, when used in powdered form, give rise to foreign body-giant cell reactions. Other compositions include demineralized bone powder and collagen. The osteogenic potential of these compositions have been found to be less than satisfactory.

The discovery of osteogenic factors and their application to bone graft substitute compositions has increased the effectiveness of the above-mentioned compositions. Although many preparations purport to be effective in bone repair in vertebrates, including higher animals such as primates, most of the experimentation done with the compositions have involved lower animals, such as mice and rats.

In light of this background, there remains a need for improved osteogenic compositions and methods that effectively induce bone growth in higher animals, including primates.

SUMMARY OF THE INVENTION

The invention provides in one preferred embodiment an osteogenic sponge composition useful for the induction of new bone growth in a mammal. This composition includes a resorbable sponge matrix material and an osteogenic factor, preferably one that preferably stimulates osteoblasts and osteoclasts, said osteogenic factor incorporated in the sponge matrix material. The resorbable sponge matrix material is desirably a three-dimensionally stable yet flexible material, facilitating its use as an implant. The osteogenic factor is usually incorporated in an amount that causes an increased rate of resorption of said sponge matrix material in a mammal. The composition also includes a particulate mineral having an average particle diameter of at least about 0.5 mm embedded in the resorbable sponge matrix material, wherein the particulate mineral present in a weight ratio of at least 4:1 relative to the resorbable sponge matrix material so as to provide a scaffold for bone ingrowth in the presence of the osteogenic factor. More preferred compositions are even more highly mineralized, for example wherein the particulate mineral is present in a weight ratio of at least about 10:1 relative to the resorbable sponge matrix material. The particulate mineral is desirably formed of a synthetic calcium phosphate ceramic or of bone, especially cortical bone. The osteogenic factor is most preferably BMP-2 or LMP, or comprises a nucleotide sequence encoding BMP-2 or LMP.

Another embodiment of the present invention provides a method for inducing bone growth in a primate. The method includes a first step of providing an osteogenic sponge composition having a resorbable sponge matrix material and an osteogenic factor that stimulates osteoblasts and osteoclasts incorporated in the sponge matrix material in an amount that causes an increased rate of resorption of the sponge matrix material in the primate. Particulate mineral having an average particle diameter of at least about 0.5 mm is embedded in said resorbable sponge matrix material and present in a weight ratio of at least 4:1 relative to the resorbable sponge matrix material, so as to provide a scaffold for bone ingrowth in the presence of the osteogenic factor. This osteogenic sponge composition is implanted in the primate in a void in which bone growth is desired, with the osteogenic sponge composition providing a scaffold for a duration sufficient for osteoid ingrowth through the void. Particularly preferred methods involve bone ingrowth to attain spinal fusions in humans.

Another preferred embodiment of the invention provides an osteogenic sponge composition effective for the induction of new bone growth in a mammal (especially a primate) that includes a carrier consisting essentially of a resorbable sponge matrix with particulate mineral embedded in the resorbable sponge matrix, wherein the particulate mineral is present in an amount constituting at least about 95% by weight of the carrier. An osteogenic factor that stimulates osteoblasts and osteoclasts is incorporated in said carrier.

A still further aspect of the invention provides a highly mineralized sponge implant device consisting essentially of a resorbable sponge matrix formed of collagen and having particulate biocompatible mineral embedded within said matrix. In this embodiment, the device is comprised 1% to 3% by weight of the collagen and 97% to 99% by weight of the particulate biocompatible mineral. In another inventive feature, an osteogenic factor can be incorporated in such an implant.

A further embodiment of the invention provides an interbody spinal fusion device that includes a load bearing member sized for insertion between adjacent vertebrae and any one of the aforementioned compositions retained by the load bearing member. Such fusion devices can be used in inventive interbody spinal fusion methods mammals, wherein the devices are appropriately implanted to facilitate spinal fusion.

A particular feature of the present invention relates to the discovery that the inclusion of an osteogenic factor, especially an osteoblast- and osteoclast-stimulating osteogenic factor, in a resorbable sponge composition causes a substantially accelerated resorption of the sponge. This rapid resorption can diminish or eliminate the capacity of the sponge composition to effectively stimulate and support new bone formation in a void filled with the sponge composition. This is particularly the case in primates, including humans, in which the rate of new bone formation is relatively slow. Objects of the present invention are to provide osteogenic sponge compositions effective for the induction of bone growth in mammals, particularly primates, including humans, and related methods and devices. These and other objects and advantages of the present invention will become apparent upon reading the descriptions herein.

DESCRIPTION OF THE PREFERRED EMBODIMENTS

Figure 1:
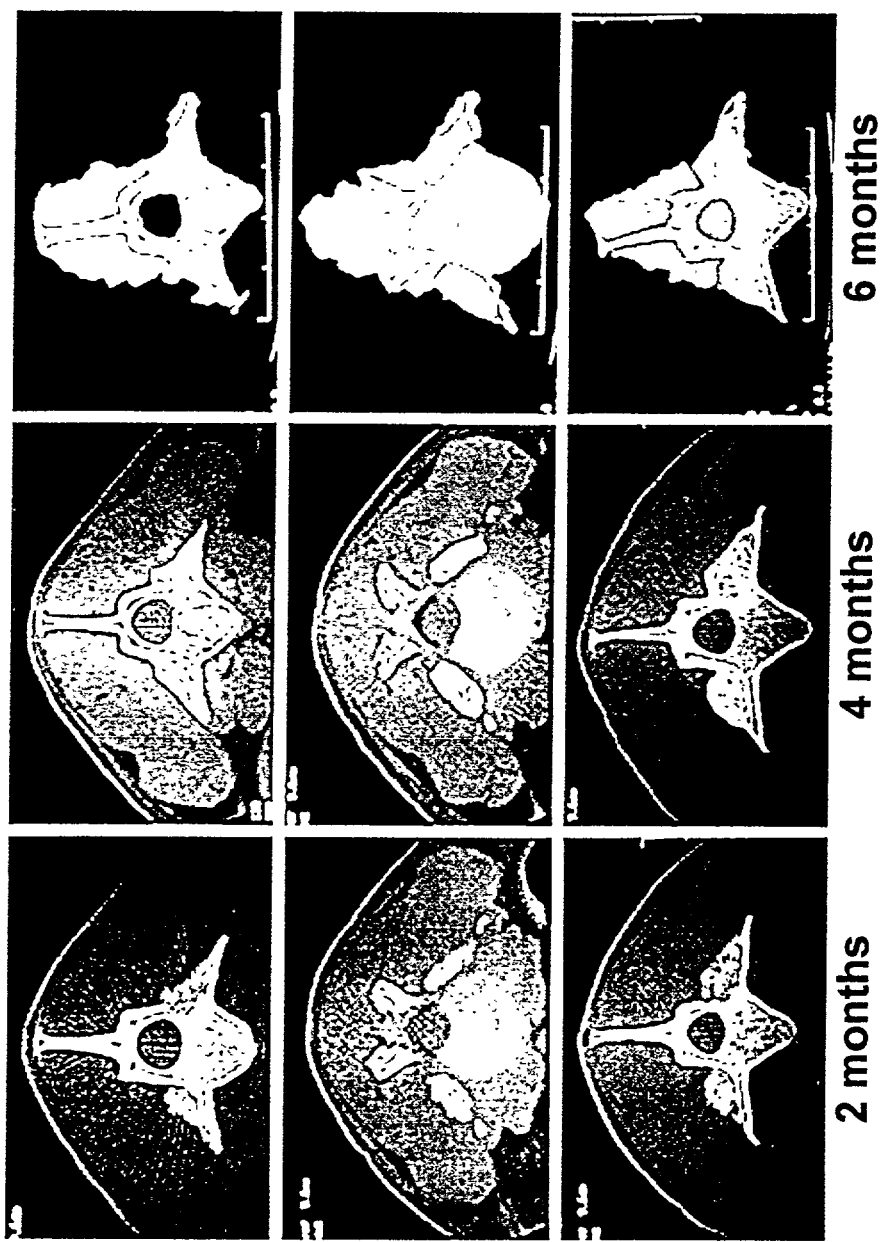
FIGS. 1 and 2 depict a digitized images of computerized tomography (CT) scans of an L4-L5 posterolateral spinal fusions performed on rhesus monkeys as described in Example 5 (top panels, section through superior transverse processes; middle panels, section through disc space; lower panels, section through inferior transverse processes).

For the purposes of promoting an understanding of the principles of the invention, reference will now be made to preferred embodiments and specific language will be used to describe the same. It will nevertheless be understood that no limitation of the scope of the invention is thereby intended, such alterations and further modifications of the invention, and such further applications of the principles of the invention as illustrated herein, being contemplated as would normally occur to one skilled in the art to which the invention relates.

As described above, the invention relates in certain aspects to osteogenic sponge compositions effective for the induction of new bone growth in mammals and methods for inducing bone growth in mammals. The present invention features osteogenic sponge compositions effective for use in primates, wherein the compositions exhibit high osteoinductive potential and provide a lasting mineral scaffold to support bone ingrowth. Such preferred compositions include a porous, resorbable sponge carrier, such as collagen in sponge form, and an osteogenic factor that stimulates the action of both osteoblasts (which biologically facilitate the formation of bone) and osteoclasts (which biologically facilitate the resorption of bone). In accordance with the present invention, it has been found that the incorporation of an effective inductive amount of an osteogenic factor, such as a bone morphogenetic protein (BMP), stimulates osteoclasts to such a level that a porous resorbable carrier is quickly resorbed and, in the absence of a high mineral component in the composition, causes the performance of the composition to suffer in some cases to the extent that the observation of substantial bone ingrowth is sporadic. Although such non-mineralized sponge compositions may be highly effective for repair of bone defects in lower animals, such as mice, that have a faster bone growth rate, they are less effective in large animals such as primates, including humans.

Accordingly, a feature of the present invention is the provision of an osteogenic composition in the form of a sponge that includes a substantial amount of a relatively slowly-resorbed mineral component that remains at the implant site after the carrier has been rapidly resorbed, in order to provide a scaffold for new bone formation that is not prematurely resorbed due to the osteoclastic potentiation by the bone morphogenic protein in the composition. The present invention also provides methods for using such osteogenic compositions in treatment of bone trauma, disease and defects, for artificial arthrodeses and for other treatment where new bone formation is desired, especially in primates, including humans.

The sponge matrix material is preferably collagenous. A wide variety of collagen materials are suitable for the sponge matrix. Naturally occurring collagens may be subclassified into several different types depending on their amino acid sequence, carbohydrate content and presence or absence of disulfide cross-links. Types I and III collagen are two of the most common subtypes of collagen. Type I collagen is present in skin, tendon and bone whereas Type III collagen is found primarily in skin. The collagen in the composition may be obtained from skin, bone, tendon, or cartilage and purified by methods known in the art. Alternatively, the collagen may be purchased commercially. The collagen in the composition is preferably Type I bovine collagen.

The collagen carrier can further be atelopeptide collagen and/or telopeptide collagen. Moreover, both non-fibrillar and fibrillar collagen may be used. Non-fibrillar collagen is collagen that has been solubilized and has not been reconstituted into its native fibrillar form.

The sponge carrier may also be formed of other natural or synthetic polymeric materials, in addition to or as an alternative to collagen. For example, the sponge carrier may be formed of gelatin (e.g. foamed gelatin), in addition collagen or as an alternative to collagen. Other natural and synthetic polymers are also known for the formation of biocompatible sponge materials, and can be used herein.

As indicated above, preferred compositions of the invention also include an osteoinductive factor, such as an osteoinductive protein or a nucleotide sequence encoding an osteoinductive protein operably associated with a promoter (e.g. provided in a vector such as a viral vector) which drives expression of the gene in the animal recipient to produce an effective amount of the protein. The osteogenic factor utilized in the present invention can be one that stimulates production or activity of osteoblasts and osteoclasts. The factor is preferably a bone morphogenetic protein (BMP) or a LIM mineralization protein (LMP), or comprises a nucleotide sequence encoding a BMP or LMP. Recombinant human BMPs are preferred, and may be commercially obtained or prepared as described and known in the art, e.g. in U.S. Pat. No. 5,187,076 to Wozney et al.; U.S. Pat. No. 5,366,875 to Wozney et al.; U.S. Pat. No. 4,877,864 to Wang et al.; U.S. Pat. No. 5,108,932 to Wang et al.; U.S. Pat. No. 5,116,738 to Wang et al.; U.S. Pat. No. 5,013,649 to Wang et al.; U.S. Pat. No. 5,106,748 to Wozney et al; and PCT Patent Nos. WO93/00432 to Wozney et al.; WO94/2693 to Celeste et al.; and WO94/26892 to Celeste et al. Further, the osteoinductive factor may be isolated from bone. Methods for isolating BMP from bone are described in U.S. Pat. No. 4,294,753 to Urist and Urist et al., PNAS 371, 1984. Recombinant human BMP-2 (rhBMP-2), recombinant human BMP-4 (rhBMP-4), recombinant human BMP-7 (rhBMP-7) or heterodimers thereof are most preferred. The osteoinductive factor may also be LIM mineralization protein (LMP) or a suitable vector incorporating a gene encoding the same operably associated with a promotor, as described in WO99/06563 (see also genbank accession No. AF095585). When such vectors are employed as osteogenic factors in accordance with the invention, they are preferably delivered in conjunction with cells, for example autologous cells from the recipient of the implant. Most preferably the vector is delivered in conjunction with autologous white blood cells derived from bone marrow or peripheral blood of the recipient. These cells may be applied to the sponge composition along with the osteogenic factor prior to implantation.

The particulate mineral component includes a natural or synthetic mineral that is effective in providing a scaffold for bone ingrowth as the resorbable carrier is resorbed. The mineral may be, for example, bone, especially cortical bone, or a synthetic bioceramic such as a biocompatible calcium phosphate ceramic. Illustrative ceramics include tricalcium phosphate, hydroxyapatite, and biphasic calcium phosphate. These mineral components may be purchased commercially or obtained or synthesized by methods known in the art.

Biphasic calcium phosphate is a particularly preferred synthetic ceramic for use in the invention. Desirably, such biphasic calcium phosphate with have a tricalcium phosphate:hydroxyapatite weight ratio of about 50:50 to about 95:5, more preferably about 70:30 to about 95:5, even more preferably about 80:20 to about 90:10, and most preferably about 85:15.

In general, the amount of mineral in the osteogenic sponge composition must be sufficient to provide a scaffold that will remain in the patient for a period of time sufficient for the formation of osteoid in the void for which bone growth is desired. Typically, this period of time will be about 6 to about 8 weeks. The minimum level of mineral that must be present in the composition is also dependent on the activity of the BMP in the composition; the higher the activity of the BMP, the greater the content of the mineral matrix required to counter the osteoclastic potentiation of the BMP. The rate of resorption of the resorbable carrier also increases as the BMP concentration increases.

In preferred aspects of the invention, the particulate mineral:resorbable sponge matrix weight ratio will be at least about 4:1, more preferably at least about 10:1. In particularly preferred sponge implants, the particulate mineral will constitute at least 95% by weight of the sponge implant. For example, highly effective sponge carrier devices are provided wherein they comprise about 97% to about 99% by weight particulate mineral and about 1% to about 3% of the collagen or other sponge-forming matrix material. Moreover, it is preferred that the mineral component have an average particle size of at least about 0.5 mm, more preferably about 0.5 mm to about 5 mm, and most preferably about 1 mm to about 3 mm.

To make the sponge implant, a collagen slurry may be formed as known and preferably is chilled to increase its viscosity to help suspend the porous particulate mineral component. The porous particulate mineral is dispersed into the collagen slurry and gently mixed. After the porous particulate mineral component is uniformly dispersed in the slurry, the slurry is poured into sterile trays or other forms and freeze dried. The sheets of composite sponge are then removed from the freeze drier and exposed to a gluteraldehyde cross-linking agent. The composite sponge formed is generally three-dimensionally stable and can be sterilized and packaged in accordance with known procedures.

The dimensions of the sponge produced may vary depending on the application. Dimensions of a typical sponge are, for example, about 10 cm (length)×7.5 cm (width)×0.35 cm (height).

As one example, BMP or other osteogenic factors may be included in the formed sponge by combining the BMP with a liquid carrier as known in the art and infusing the liquid into the sponge.

As further enhancements of the compositions of the present invention, those skilled in the art will readily appreciate that other osteogenic enhancing factors may be incorporated into the composition. Such additional factors include host compatible osteogenic progenitor cells, autographic bone marrow, allographic bone marrow, transforming growth factor-β, fibroblast growth factor, platelet-derived growth factor, insulin-like growth factor, microglobulin-β, antibiotics and steroids.

In yet another aspect of the invention, methods for inducing bone growth in mammals are provided. The methods include providing the above-described osteogenic sponge composition and implanting the composition at a site at which bone growth is desired, e.g., to treat a disease, defect or location of trauma, and/or to promote artificial arthrodesis. The hydrated sponge composition may be rolled up prior to packing the sponge into the implantation site.

Once in place, the osteogenic sponge composition will effectively induce and support ingrowth of bone into the desired area even in a primate such as a human that exhibits a relatively slow rate of bone formation compared to smaller mammals, such as rodents or rabbits. Although the collagen carrier is resorbed relatively quickly, the substantial mineral component remains as a scaffolding to support new bone growth in and through the desired area.

The above osteogenic sponge compositions of the present invention are especially advantageous when used in bones or bone portions that exhibit only low to moderate vascularization. Such low to moderate vascularized regions exhibit low rates of bone formation so rapid resorption of a carrier poses a problem. Examples of low to moderate vascularized sites include, for example, transverse processes or other posterior elements of the spine.

An especially preferred use of the sponge compositions of the present invention is as an implant to promote arthrodesis between vertebrae in spinal fusions in humans or other primates, including interbody, posterior and/or posterolateral fusion techniques. Although the rate of bone formation in the primate spine is relatively slow overall and thus will benefit generally from the present invention, the elements to be fused in posterior and posterolateral fusions exhibit particularly low levels of vascularization and thus fusions of these elements are expected to benefit markedly from the invention.

Moreover, the osteogenic sponge compositions can be incorporated with a load-bearing member used in a spinal fusion, including hollow spinal cages, dowels or other devices known in the art having a pocket, chamber or other mechanism for retaining the osteogenic sponge composition. The load-bearing member desirably will have a compressive strength of at least about 10,000 N. Suitable such load bearing members are described, for example in U.S. Pat. Nos. 5,522,899, 5,785,710, 5,776,199 and 5,814,084, each of which is hereby incorporated by reference in its entirety.

Reference will now be made to specific examples using the processes described above. It is to be understood that the examples are illustrative and not limiting of the invention.

EXAMPLE 1

Preparation of Collagen Sponge/Bone Particle Composite 12 grams of deproteinized cortical bone chips, 1-3 mm in size, were added to 12 grams of collagen slurry (0.192 grams of collagen). This composite slurry was poured into a 7.5 cm×10.0 cm mold, freeze dried, double sterile packaged, and sterilized by ETO gas sterilization.

EXAMPLE 2

Preparation of Collagen Sponge/Synthetic Ceramic Composite 12 grams of biphasic calcium phosphate particles, 1 mm in diameter, were added to 12 grams of collagen slurry (0.192 grams of collagen). This composite slurry was poured into a 7.5 cm×10.0 cm mold, freeze dried, double sterile packaged, and sterilized by ETO gas sterilization.

EXAMPLE 3

Preparation of Collagen Sponge/Bone Particle Composite 12 grams of deproteinized cortical bone chips, 1-3 mm in size. were added to 24 grams of collagen slurry (0.192 grams of collagen). This composite slurry was poured into a 7.5 cm×10.0 cm mold, freeze dried, double sterile packaged, and sterilized by ETO gas sterilization.

EXAMPLE 4

Preparation of Collagen Sponge/Synthetic Ceramic Composite 12 grams of biphasic calcium phosphate particles, 1 mm in diameter, were added to 24 grams of collagen slurry (0.192 grams of collagen). This composite slurry was poured into a 7.5 cm×10.0 cm mold, freeze dried, double sterile packaged, and sterilized by ETO gas sterilization.

EXAMPLE 5

L4-L5 Posterolateral Intertransverse Process Spinal Fusion Study

The present study was performed to determine the effect of the osteogenic sponge compositions of the present invention on spinal fusion.

The experimental group included two adult rhesus monkeys (*Macaca mulatta*). The monkeys were anesthetized with 3-5 mg/kg telazol intramuscularly (i.m.). The anesthesia was maintained with 1.5-2.0% isoflurane. After anesthesia was achieved, animals were shaved, prepared with betadine and sterily draped. The surgical site was infiltrated with 10-15 ml of 0.25% marcaine to aid with immediate postoperative analgesia. A midlineposterior skin incision was made over the lumbar spine. The paraspinal muscles were reflected using elevators, exposing the lamina and the transverse processes of the L4 and L5 vertebral bodies. The transverse processes of the two vertebrae to be fused were decorticated with an electric burr.

Composite sponges, having dimension of 3.5 cm×1.4 cm×0.35 cm, were prepared using techniques as described in Examples 1 and 2. The sponges included, on a weight basis, 97% biphasic calcium phosphate (15% hydroxyapatite and 85% tricalcium phosphate, 1 mm particle size) and 3% collagen. Recombinant human BMP-2 (rhBMP-2) was prepared at a concentration of 3.0 mg/ml in a buffered solution. Each sponge was infused with 1.5 ml of the rhBMP-2 solution.

The sponges were placed in the paraspinal bed directly on top of and bridging the two adjacent transverse processes. The sponges were placed bilaterally, with two sponges (one on top of the other) on each side of the spine, resulting in a total dose of 9 mg rhBMP-2 per implant site. The animals were allowed to recover and move around ad libitum without restrictions during the study period.

The spines were manually assessed for fusion upon sacrifice (2, 4 and 6 months) and determined to be fused based upon the absence of motion during attempted bending, and presence of histological bridging bone.

Figure 2:
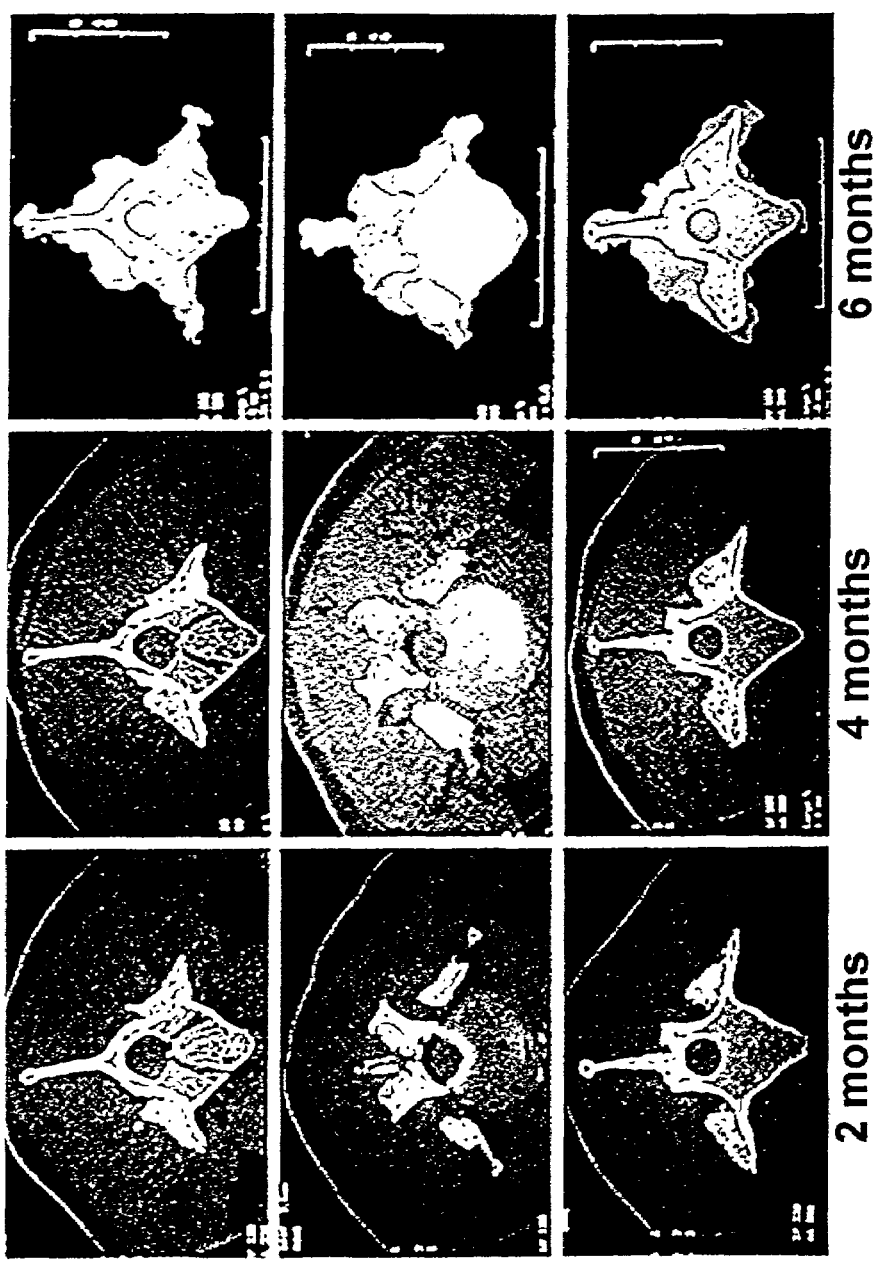

The fusions were also evaluated by CT scan at 2, 4 and 6 months after implantation. FIGS. 1 and 2 show the CT scans for each subject studied. FIGS. 1 and 2 demonstrate the sequence of events that occur within the composite sponge carrier loaded with rhBMP-2. On the far left of the figures are three CT sections equally spaced throughout the fusion mass at 2 months post-operative, showing that resorption of the composite sponge is just about complete due to the lack of radiopacity of the ceramic granules. The three middle CT sections show these same three CT sections at four months with increased bone deposition where the carrier once resided. The composite sponge has maintained the space within the soft tissue site for a sufficient enough period of time for the desired volume of new bone deposition to occur. Finally, the far right three CT scans show even further bone deposition, remodeling and maturation with the formation of outer cortices around the periphery of the fusion masses by six months.

What is claimed is:

1. An osteogenic sponge composition comprising:
   a highly mineralized sponge implant device, said device being three-dimensionally stable but flexible, said device exhibiting sufficient flexibility to be rolled up when hydrated, said device consisting essentially of a resorbable sponge matrix formed of lyophilized collagen and having particulate biocompatible mineral embedded within said matrix, said device comprised 1% to 3% by weight of the lyophilized collagen and 97% to 99% by weight of the particulate biocompatible mineral, said resorbable sponge matrix having been prepared by a process comprising freeze-drying a slurry including the collagen and particulate biocompatible mineral; and
   an osteogenic factor effective to stimulate both osteoblasts and osteoclasts when administered to a human, and wherein said osteogenic factor is incorporated into said sponge implant device in an amount to stimulate the osteoclasts to cause an increase in the rate of resorption of said resorbable sponge matrix when said sponge implant device is implanted in a human; and
   wherein said particulate biocompatible mineral is resorbed more slowly than said resorbable sponge matrix when said sponge implant device is implanted in a human and thereby provides a scaffold for bone ingrowth that remains after said resorbable sponge matrix is resorbed.

2. The osteogenic sponge composition of claim 1, wherein the particulate biocompatible mineral comprises bone particles.

3. The osteogenic sponge composition of claim 1, wherein the particulate biocompatible mineral includes a synthetic ceramic.

4. The osteogenic sponge composition of claim 3, wherein the ceramic material includes a calcium phosphate ceramic.

5. The osteogenic sponge composition of claim 4, wherein the calcium phosphate ceramic is biphasic calcium phosphate.

6. An interbody spinal fusion device, comprising:
   a load bearing member sized for insertion between adjacent vertebrae; and
   a composition according to any of claims 1-5 retained by said load bearing member.

7. The osteogenic sponge composition of claim 1, wherein the collagen comprises telopeptide collagen.

8. The osteogenic sponge composition of claim 7, wherein the osteogenic factor comprises a bone morphogenic protein.

9. The osteogenic sponge composition of claim 8, wherein the bone morphogenic protein comprises BMP-2 or BMP-7.

10. The osteogenic sponge composition of claim 9, wherein the bone morphogenic protein comprises BMP-2.

11. The osteogenic sponge composition of claim 1, wherein the particulate biocompatible mineral has an average particle diameter of greater than about 0.5 millimeters.

12. The osteogenic sponge composition of claim 1, wherein the particulate biocompatible mineral has an average particle diameter in the range of about 0.5 millimeters to about 5 millimeters.

13. The osteogenic sponge composition of claim 12, wherein the particulate biocompatible mineral has an average particle diameter of about 1 millimeter to about 3 millimeter.

14. An osteoinductive composition effective for the induction of new bone growth in a human patient, comprising a highly mineralized sponge implant device, said device being three-dimensionally stable but flexible, said device exhibiting sufficient flexibility to be rolled up when hydrated, said device comprising a resorbable sponge matrix and a particulate biocompatible mineral embedded within said matrix, said device comprised at least 95% by weight of the particulate biocompatible mineral;
    wherein said resorbable sponge matrix comprises collagen, and said particulate biocompatible mineral comprises a calcium phosphate ceramic or bone; wherein said resorbable sponge matrix has been prepared by a process comprising freeze-drying a slurry including the collagen and particulate biocompatible mineral; and
    an osteogenic factor effective to stimulate both osteoblasts and osteoclasts when administered to a human, and wherein said osteogenic factor is incorporated into said sponge implant device in an amount to stimulate the osteoclasts to cause an increase in the rate of resorption of said resorbable sponge matrix when said sponge implant device is implanted in a human; and
    wherein said particulate biocompatible mineral is resorbed more slowly than said resorbable sponge matrix when said sponge implant device is implanted in a human and thereby provides a scaffold for bone ingrowth that remains after said resorbable sponge matrix is resorbed.

15. The osteoinductive composition of claim 14, wherein the osteogenic factor comprises a bone morphogenic protein.

16. The osteoinductive composition of claim 15, wherein the bone morphogenic protein comprises BMP-2 or BMP-7.

17. The osteoinductive composition of claim 16, wherein the bone morphogenic protein comprises BMP-2.

18. The osteogenic sponge composition of claim 1, wherein said resorbable sponge matrix comprises fibrillar collagen.

19. An osteogenic sponge composition effective for the induction of new bone growth in a human, comprising:
    a highly mineralized sponge implant device, said device being three-dimensionally stable but flexible, said device comprising a resorbable sponge matrix formed of collagen and having particulate biocompatible mineral embedded within said matrix, said device comprised 1% to 3% by weight of the collagen and 97% to 99% by weight of the particulate biocompatible mineral, said device prepared by providing a slurry including the collagen and the particulate biocompatible mineral, freeze-drying the slurry to form a dried sponge material, and crosslinking the dried sponge material to result in a three-dimensionally stable but flexible device, said device exhibiting sufficient flexibility to be rolled up when hydrated; and
    an osteogenic factor effective to stimulate both osteoblasts and osteoclasts when administered to a human, and wherein said osteogenic factor is incorporated into said sponge implant device in an amount to stimulate the osteoclasts to cause an increase in the rate of resorption of said resorbable sponge matrix when said sponge implant device is implanted in a human; and
    wherein said particulate biocompatible mineral is resorbed more slowly than said resorbable sponge matrix when said sponge implant device is implanted in a human and thereby provides a scaffold for bone ingrowth that remains after said resorbable sponge matrix is resorbed.

20. An osteogenic composition effective for the induction of new bone growth in a human patient, comprising:
    a highly mineralized sponge implant device, said device being three-dimensionally stable but flexible, said device comprising a resorbable sponge matrix and a particulate biocompatible mineral embedded within said matrix, said device comprised 1% to 3% by weight of a material forming said sponge matrix, and 97% to 99% by weight of the particulate biocompatible mineral, wherein said resorbable sponge matrix comprises collagen, said particulate biocompatible mineral comprises biphasic calcium phosphate, said resorbable sponge matrix has been prepared by a process comprising freeze-drying a slurry including the collagen and particulate biocompatible mineral, and said device exhibiting sufficient flexibility to be rolled up when hydrated; and
    an osteogenic factor effective to stimulate both osteoblasts and osteoclasts when administered to a human, and wherein said osteogenic factor is incorporated into said sponge implant device in an amount to stimulate the osteoclasts to cause an increase in the rate of resorption of said resorbable sponge matrix when said sponge implant device is implanted in a human; and
    wherein said particulate biocompatible mineral is resorbed more slowly than said resorbable sponge matrix when said sponge implant device is implanted in a human and thereby provides a scaffold for bone ingrowth that remains after said resorbable sponge matrix is resorbed.

* * * * *